United States Patent [19]

(12) United States Patent  
Smith et al.

(10) Patent No.: US 8,542,962 B2  
(45) Date of Patent: Sep. 24, 2013

(54) PRECONDITIONED ILLUMINATOR SYSTEM AND METHOD

(75) Inventors: Ronald T. Smith, Irvine, CA (US); Dean Y. Lin, Chino Hills, CA (US); Jack R. Auld, Laguna Niguel, CA (US); Timothy C. Ryan, Laguna Hills, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 892 days.

(21) Appl. No.: 12/540,755

(22) Filed: Aug. 13, 2009

(65) Prior Publication Data

US 2010/0042080 A1 Feb. 18, 2010

Related U.S. Application Data

(60) Provisional application No. 61/088,484, filed on Aug. 13, 2008.

(51) Int. Cl.  
*G02B 6/32* (2006.01)  
*A61B 1/07* (2006.01)

(52) U.S. Cl.  
USPC ............................................. 385/33; 362/572

(58) Field of Classification Search  
USPC ................................. 362/572–575  
See application file for complete search history.

(56) References Cited

U.S. PATENT DOCUMENTS

| 5,224,942 | A | * | 7/1993 | Beuchat et al. ................. 606/2.5 |
| 5,784,508 | A | * | 7/1998 | Turner ............................. 385/31 |
| 6,102,905 | A | * | 8/2000 | Baxter et al. .................... 606/15 |
| 7,499,624 | B2 | | 3/2009 | Dacquay et al. |
| 7,618,177 | B2 | | 11/2009 | Cazzini |
| 7,731,710 | B2 | | 6/2010 | Smith |
| 8,012,146 | B2 | | 9/2011 | Hickingbotham |
| 8,152,798 | B2 | | 4/2012 | Smith |

(Continued)

OTHER PUBLICATIONS

U.S. Appl. No. 11/354,615, filed Feb. 15, 2006.

(Continued)

*Primary Examiner* — Jerry Rahll  
(74) *Attorney, Agent, or Firm* — Darien Reddick (57) ABSTRACT

Embodiments of endo-illuminators and related methods are disclosed. One embodiment of an illuminator can comprise a cannula defining a passage, an optical element disposed at an end of the cannula, and an optical fiber running through the passage with the distal end of the optical fiber in contact with the optical element. The optical fiber includes at least a heat preconditioned distal portion that terminates in the distal end that is in contact with the optical element. One embodiment of a method can comprise inserting an optical fiber through a proximal portion of a cannula and optical element assembly until the distal end of the optical fiber contacts the optical element, heating a distal portion of the optical fiber to between a softening temperature and a melting temperature for a period of time to cause the distal portion to axially shrink and moving the optical element so that the optical element is in contact with the distal end of the optical fiber when the distal portion of the optical fiber has axially shrunk. Moving the optical element so that the optical element is in contact with the distal end of the optical fiber when the distal portion of the optical fiber has axially shrunk can comprise applying a force to the cannula and optical element assembly to maintain the optical element in continuous contact with the distal end of the optical fiber while the optical fiber axially shrinks.

20 Claims, 6 Drawing Sheets

(56) References Cited

U.S. PATENT DOCUMENTS

| | | |
|---|---|---|
| 2003/0219202 A1 | 11/2003 | Loeb et al. |
| 2006/0184162 A1* | 8/2006 | Smith .............................. 606/4 |
| 2009/0161384 A1 | 6/2009 | Smith |
| 2010/0268203 A1 | 10/2010 | Smith |
| 2011/0037949 A1 | 2/2011 | Papac et al. |
| 2011/0038174 A1 | 2/2011 | Papac et al. |
| 2011/0110114 A1 | 5/2011 | Papac et al. |
| 2011/0112377 A1 | 5/2011 | Papac et al. |
| 2011/0149591 A1 | 6/2011 | Smith |
| 2011/0149592 A1 | 6/2011 | Artsyukhovich et al. |

OTHER PUBLICATIONS

Papac et al., Wavelength Converting Illumination Probe, U.S. Appl. No. 12/963,733, filed Dec. 9, 2010, 32 pages.

Auld et al., Ophthalmic Endoilluminators With Directed Light, U.S. Appl. No. 13/241,427, filed Sep. 23, 2011, 20 pages.

Smith et al., Preconditioned Illuminator System and Method, U.S. Appl. No. 13/430,235, filed Mar. 26, 2012, 30 pages.

Smith, High Throughput Endo-Illuminator Probe, U.S. Appl. No. 11/354,615, filed Feb. 15, 2006, 31 pages.

\* cited by examiner

PRECONDITIONED ILLUMINATOR SYSTEM AND METHOD

This application claims priority to U.S. Patent Application Ser. No. 61/088,484 filed on Aug. 13, 2008.

TECHNICAL FIELD OF THE INVENTION

Systems and methods disclosed herein relate generally to surgical instrumentation. In particular, the systems and methods relate to surgical instruments for illuminating an area during eye surgery. Even more particularly, the systems and methods relate to illuminators for illumination of a surgical field that are preconditioned to relieve stress.

BACKGROUND OF THE INVENTION

In ophthalmic surgery, and in particular in vitreo-retinal surgery, it is desirable to use a wide-angle surgical microscope system to view as large a portion of the retina as possible. Wide-angle objective lenses for such microscopic systems exist, but they require a wider illumination field than that provided by the cone of illumination of a typical fiber-optic probe. As a result, various technologies have been developed to increase the beam spreading of the relatively incoherent light provided by a fiber-optic illuminator. These known wide-angle illuminators can thus illuminate a larger portion of the retina as required by current wide-angle surgical microscope systems.

Current wide-angle illuminators can experience run-away heating that degrades the performance of the illuminator. Run-away heating occurs when the cannula of an illuminator absorbs light from the optical fiber running through the illuminator and, consequently, increases in temperature. As the cannula heats, the optical fiber may begin to deform, causing even more light to be incident on the cannula, increasing the temperature of the cannula further and, hence, increasing the deformation in the optical fiber. This cycle can lead to catastrophic failure of the illuminator.

SUMMARY

The various embodiments of the method and system of the present invention provide for an illuminator that is resistant to run-away heat deformation. In general, the optical fiber of the illuminator undergoes heat preconditioning at its distal portion to relieve axial stress at the distal portion prior to or in lieu of the distal portion being fixed in place relative to other components of the illuminator. Such preconditioned illuminators can be used for longer periods of time using more intense light than traditional illuminators.

According to one embodiment, an illuminator can comprise a cannula defining a passage, an optical element disposed at a distal end of the cannula, and an optical fiber running through the passage with the distal end of the optical fiber in contact with the optical element. The optical fiber includes at least a heat preconditioned distal portion that terminates in the distal end that is in contact with the optical element.

One embodiment of preconditioning an illuminator can comprise inserting an optical fiber through a proximal portion of a cannula/optical element assembly until the distal end of the optical fiber contacts the optical element, heating a distal portion of the optical fiber to between a softening temperature and a melting temperature for a period of time to cause the distal portion to axially shrink and moving the optical element so that the optical element is in contact with the distal end of the optical fiber when the distal portion of the optical fiber has axially shrunk. Moving the optical element so that the optical element is in contact with the distal end of the optical fiber when the distal portion of the optical fiber has axially shrunk can comprise applying a force to the cannula/optical element assembly to maintain the optical element in continuous contact with the distal end of the optical fiber while the optical fiber axially shrinks. In a vertical arrangement, this can be done through the force of gravity.

Yet another embodiment of an illuminator method comprises inserting an optical fiber through a proximal portion of a cannula until the distal end of the optical fiber contacts a lens, vertically aligning the cannula with an opening defined by a heating member, lowering the heating member until the cannula is inserted a desired insertion depth in the opening, heating a distal portion of the optical fiber to between a softening temperature and a melting temperature for a period of time to cause the distal portion to axially shrink and allowing the cannula to move so that the lens remains in contact with the distal end of the optical as the distal portion axially shrinks.

BRIEF DESCRIPTION OF THE FIGURES

A more complete understanding of the various embodiments and the advantages thereof may be acquired by referring to the following description, taken in conjunction with the accompanying drawings in which like reference numbers indicate like features and wherein.

DETAILED DESCRIPTION OF THE INVENTION

Preferred embodiments of the present invention are illustrated in the FIGURES, like numerals being used to refer to like and corresponding parts of the various drawings.

Figure 1:
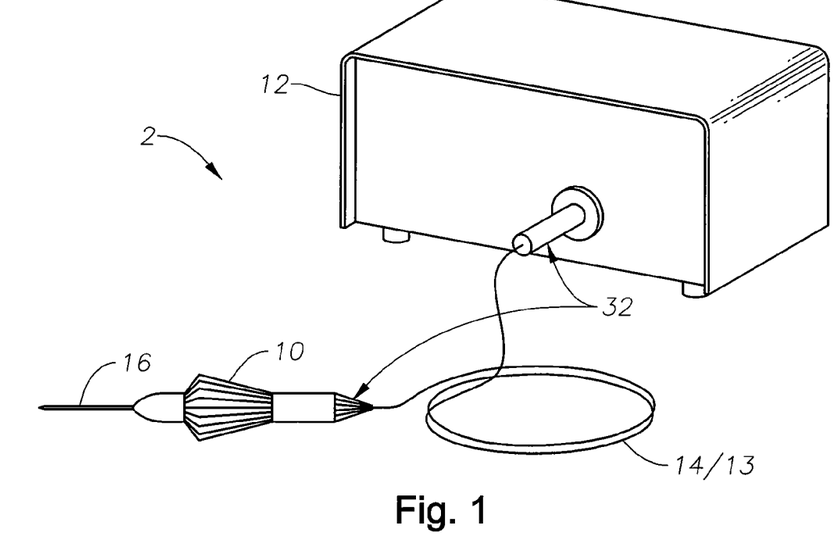
FIG. 1 is a simplified diagram of a surgical system.

FIG. 1 is a simplified diagram of a surgical system 2 comprising a handpiece 10 for delivering a beam of light, which can be incoherent light, from a light source 12 through cable 14 to the distal end of a stem (cannula) 16. Handpiece 10 can be any surgical handpiece as known in the art, such as the Revolution-DSP™ handpiece sold by Alcon Laboratories, Inc. of Fort Worth, Tex. Light source 10 can be a xenon light source, a halogen light source, or any other light source capable of delivering relatively incoherent light which can be transmitted through a fiber optic cable. By way of example, but not limitation, light source 10 can be an Accurus High Brightness Illuminator or a Constellation Illuminator, both manufactured and sold by Alcon Laboratories, Inc. Cable 14 can comprise a proximal optical fiber 13 of any gauge fiber optic cable as known in the art, but proximal optical fiber 13 is preferably a 20 or 25 gauge compatible fiber. Cannula 16 can be a small gauge cannula, preferably on the order of 19, 20, 23 or 25 gauge, as known to those having skill in the art. Stem 16 can be stainless steel or a suitable biocompatible polymer (e.g., PEEK, polyimide, etc.) as known to those having skill in the art. Cannulla 16 is configured to house a distal optical fiber 20, as is more clearly illustrated in FIG. 2. Coupling system 32 can comprise an optical fiber connector at the proximal end of optical cable 14 to optically couple light source 12 to proximal optical fiber 13 within optical cable 14.

The proximal optical fiber 13, distal optical fiber 20 and/or stem 16 can be operably coupled to the handpiece 10, for example, via an adjusting mechanism. The adjusting mechanism can comprise, for example, a simple push/pull mechanism as known to those having skill in the art. Light source 12 can be operably coupled to handpiece 10 (i.e., optically coupled to proximal optical fiber 13 within optical cable 14) using, for example, standard SMA (Scale Manufacturers Association) optical fiber connectors at the proximal end of fiber optic cable 14. This allows for the efficient transmission of light from the light source 12 to a surgical site through proximal optical fiber 13, passing within handpiece 10, through tapered section 26 (whether separate or integral to distal optical fiber 20) and optical fiber 20 to emanate from the distal end of distal optical fiber 20 and stem 16. Light source 12 may comprise filters, as known to those having skill in the art, to reduce the damaging thermal effects of absorbed infrared radiation originating at the light source. The light source 12 filter(s) can be used to selectively illuminate a surgical field with different colors of light, such as, for example, to excite a surgical dye.

Figure 2:
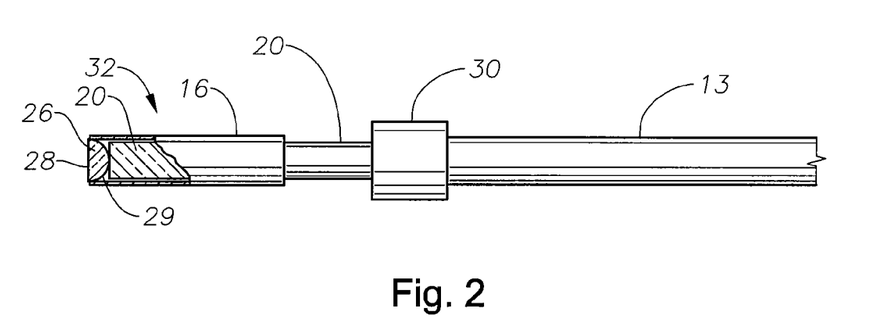
FIG. 2 is a diagrammatic representation of a portion of an illuminator.

FIG. 2 is a diagrammatic representation of a portion of one embodiment of an endo-illuminator of the present invention including a cannula 16, a distal optical fiber 20 and a proximal optical fiber 13. Distal optical fiber 20 can be optically coupled to proximal optical fiber 13 at coupling 30, which can, in turn, be optically coupled to light source 12 (see FIG. 1) to receive light from the light source 12. Proximal optical fiber 13 can be a larger diameter, small NA (e.g., 0.5 NA) optical fiber, such as a 20 gauge compatible optical fiber. Distal optical fiber 20 can be a high numerical aperture ("NA"), smaller diameter (e.g., 25 gauge compatible) optical fiber or light pipe (e.g., cylindrical light pipe) located downstream of the proximal optical fiber. An optical element 26 is in contact with the distal end of distal optical fiber 20. One or more of proximal optical fiber 13 or distal optical fiber 20 may include a protective sheath made out of a suitable material, such as PVC or other material.

Fiber(s) 20 is terminated by optically coupling to optical element 26. Optical element 26 can be an optical grade sapphire diffuser having a hemispherical or slightly larger than hemispherical shape. Optical element 26 can comprise a polished flat surface 28 at the distal end of stem 16 (i.e., facing out towards a surgical field) and a hemispherical surface 29 facing the distal end of fiber 20. Optical element 26 is sized for housing within stem 16 (e.g., a 19 to 30 gauge cannula). For example, optical element 26 can have a diameter of about 0.75 mm to about 0.4 mm. The flat surface 28 of optical element 26 can be co-incident with the open aperture at the distal end of stem 16.

The embodiment of the high throughput endo-illuminator of this invention illustrated in FIG. 2 comprises a low-NA, larger diameter proximal optical fiber 13 optically coupled to a tapered, high-NA, smaller diameter distal optical fiber 20. The proximal optical fiber 13 can be a 0.50 NA plastic fiber (e.g., to match the NA of the light source 12), having a polymethyl methacrylate (PMMA) core and a 0.030" (750 micron) core diameter, or another such comparable fiber as known to those having skill in the art. For example, such a fiber is compatible with the dimensions of the focused light spot from a 20 gauge light source 12, such as the ACCURUS® illuminator manufactured by Alcon Laboratories, Inc. of Fort Worth, Tex. As one example, suitable fibers for the proximal optical fiber 13 of the embodiments of this invention are produced by Mitsubishi (Super-Eska fiber), which can be purchased through Industrial Fiber Optics, and Toray, which can be purchased through Moritex Corporation.

Suitable fibers for the distal optical fiber 20 (downstream fiber) are Polymicro's High OH (FSU), 0.66 NA, silica core/Teflon AF clad optical fiber, having a core diameter that can be custom-made to required specifications and Toray's PJU-FB500 0.63 NA fiber (486 micron core diameter). Proximal optical fiber 13 and distal optical fiber 20 can be optically coupled together using any suitable mechanism known to those skilled in the art.

In the embodiment of FIG. 2, the endo-illuminator comprises a proximal optical fiber 13 coupled to a distal optical fiber 20 at a coupling 30. Various methods of coupling optical fibers are described in U.S. patent application Ser. No. 11/354,615 entitled "High Throughput Endo-Illuminator Probe", filed Feb. 15, 2006, by Alcon Research, Ltd., which is hereby fully incorporated by reference herein.

Cannula/optical element assembly 32 can be formed by selecting a cannula 16 of a desired diameter, such as a 23 gauge or 25 gauge cannula, selecting an optical element material that is slightly larger than the inner diameter cannula 16 and press fitting the optical element material into the cannula. For example, a sapphire ball can be selected and press fit into the distal end of cannula 16. The optical element material can then be ground to a desired shape. In one embodiment, for example, the sapphire ball (and potentially the end of the cannula) can be ground away until the remaining optical element 26 is slightly larger than hemispherical.

According to one method of assembly, the distal optical fiber 20 is slid into the proximal end of cannula 16 until the distal end of distal optical fiber 20 contacts the optical element 26. If the cannula 16 were to be bonded at this point to optical fiber 20 without preconditioning optical fiber 20, the resulting device is more susceptible to experience runaway heating and catastrophic failure during use. This results because plastic optical fiber is created through a drawing process that stretches the fiber axially before it hardens, causing potential energy to be stored in the fiber. When the fiber is heated and the softening point reached (around 105©)), the potential energy is released by axial shrinking and lateral swelling of the fiber.

When a high-luminance xenon light is coupled to the fiber, a significant amount of luminous flux passes through the distal end of the probe through optical element 26 to illuminate the retina. However, from distal fiber 20, some amount may be absorbed by cannula 16, causing the distal end of cannula 16 and consequently the distal portion of distal fiber 20 to increase in temperature. If the temperature becomes high enough, the distal portion of distal fiber 20 will soften and axially shrink. Because the proximal end of the cannula is bonded to the distal fiber 20, the distal end of distal fiber 20 will tend to pull away from the optical element 26. This will cause more light to be absorbed by the cannula, which can cause a runaway cycle of thermal deformation to occur. This phenomenon is illustrated in FIG. 3.

Figure 3:
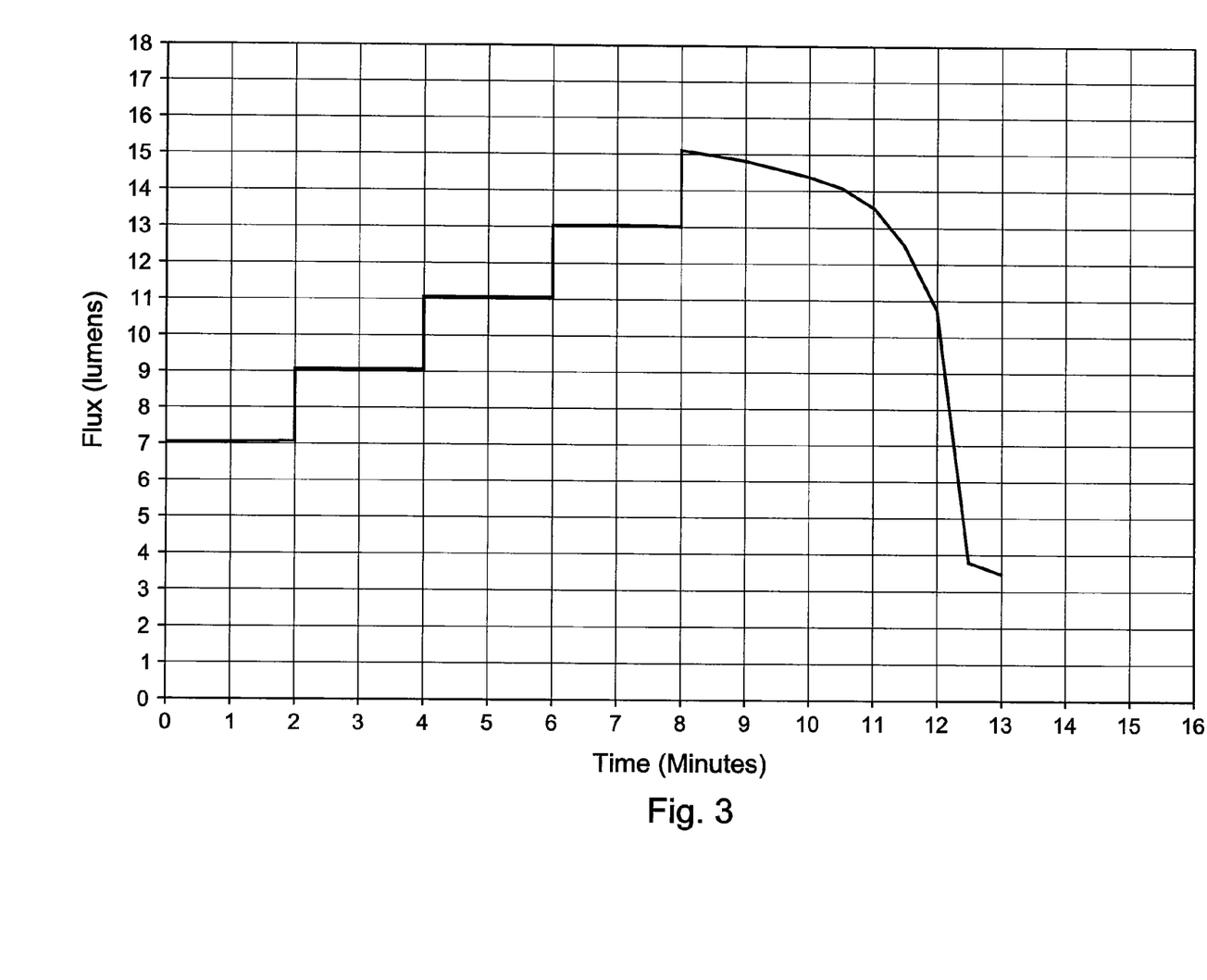
FIG. 3 is a graph showing data for run-away thermal deformation.

FIG. 3 is a graph illustrating flux over time through a cannula 16 in which cannula 16 is bonded to distal fiber 20 without preconditioning. Over time the luminous flux provided by the source light gradually increases and the output of the probe increases correspondingly. However, at 8 minutes, the flux of the source light becomes large enough to cause softening of the distal fiber 20, causing distal fiber 20 to begin shrinking axially. As the distal end of distal fiber 20 moves away from optical element 26, the output of the probe begins to gradually decrease and then, at around point 11 minutes, falls off precipitously, indicating catastrophic failure of the probe.

To prevent such failure, distal optical fiber 20 can be preconditioned to release potential energy, thereby reducing or eliminating runaway thermal deformation. To precondition the distal optical fiber 20, cannula 16 is not bonded to fiber 20 after optical fiber 20 is brought in contact with optical element 26. Instead, distal optical fiber 20 is heated to or above its softening point, but below its melting point for a defined period. This causes at least the distal portion of fiber 20 (a portion of fiber 20 starting at the distal end and ending at any point prior to the proximal end of the cannula) to shrink axially and expand laterally. Because distal fiber 20 is not yet bonded to cannula 16, optical element 26 and cannula 16 will move with optical fiber 20 as it shrinks axially. Consequently, potential energy can be released while fiber 20 remains in contact with optical element 26.

Figure 4A:
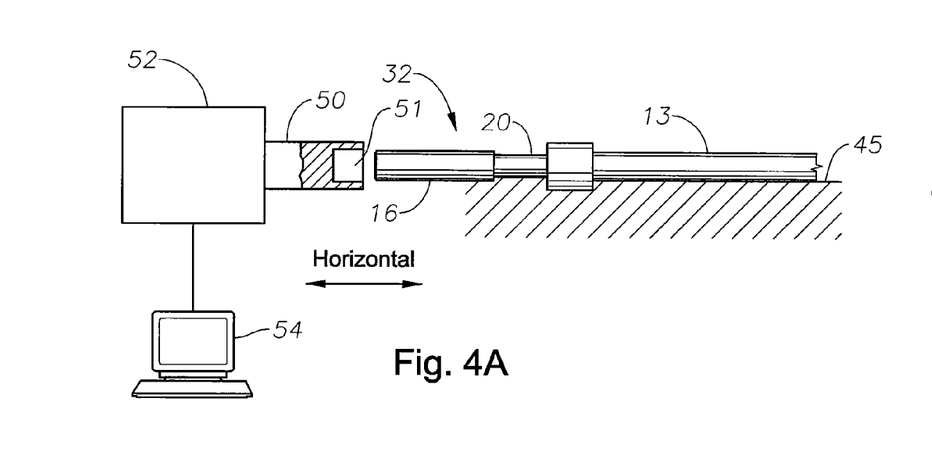
FIG. 4A is a diagrammatic representation of one embodiment of a system for preconditioning an illuminator.

FIG. 4A is a diagrammatic representation of an embodiment of a fixture for preconditioning a fiber of an endo-illuminator in accordance with the teachings of the present invention. In the embodiment shown in FIG. 4A, proximal fiber 13 is coupled to distal fiber 20 and the cannula and optical element assembly 32 is already assembled. Distal fiber 20 is inserted into cannula 16 until the distal end of distal fiber 20 contacts the optical element 26 (shown in FIG. 2). A portion of the endo-illuminator can be clamped or otherwise secured to a work surface 45. A heating member 50 can be used to heat a distal portion of the cannula 16 and optical element assembly 32. Heating member 50 can be made of any suitable material including, but not limited to, metals and ceramics, that can be heated to a desired temperature. Heating of heating member 50 can occur by, for example, running a current through resistors in heating member 50, preheating heating member 50 from another heat source or otherwise heating heating member 50 in a way known to those skilled in the art. Heating member 50 can have any suitable shape and size. According to one embodiment, heating member 50 can be a metal cylinder having an axial opening 51 with an inner diameter that is slightly larger than the outer diameter of cannula 16. The axial opening 51 can extend partially or completely through the length of heating member 50. Heating member 50 can be coupled to a computer controlled translation stage 52 that allows heating member 50 to translate along at least one axis for positioning. A computer 54 can control movement of stage 52.

Figure 4B:
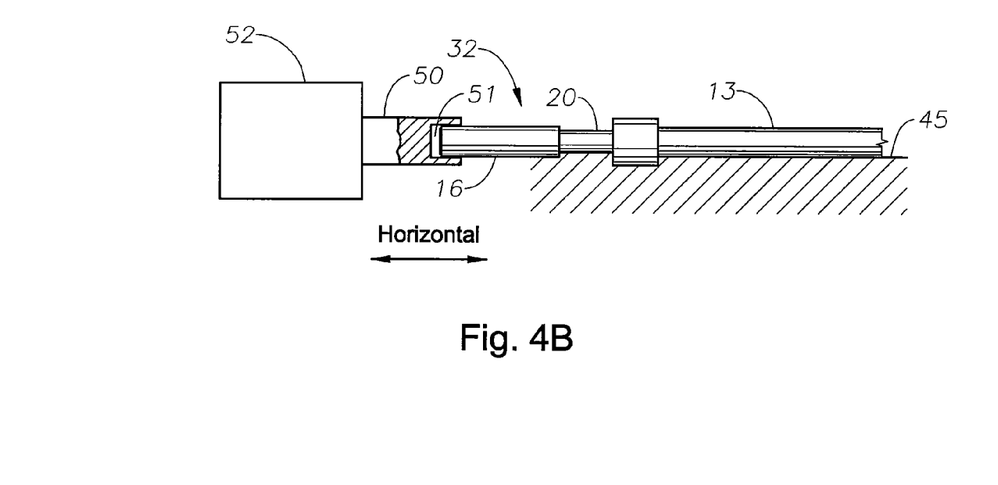
FIG. 4B is a diagrammatic representation of one embodiment of an arrangement during preconditioning an illuminator.

FIG. 4B is a diagrammatic representation of an embodiment of an arrangement for heating of cannula 16/optical element assembly 32. The opening in heating member 50 can be axially aligned with cannula 16. This can be done using, for example, cameras. Heating member 50 is then moved over some or all of cannula 16 to a desired insertion depth. Cannula 16 remains inserted in heating member 50 for a desired dwell time. To save time, heating member 50 is preferably heated to a desired temperature prior to insertion of cannula 16. However, in other embodiments, heating member 50 may be heated after insertion of cannula 16. A small force can be applied to cannula 16 as it is heated to move cannula 16 as the distal fiber 20 axially shrinks, in a direction so as to keep optical element 26 in contact with the distal end of distal fiber 20. However, the force can be limited to prevent or reduce concavity at the distal end of distal fiber 20 as optical element 26 pushes against distal fiber 20.

Figure 5:
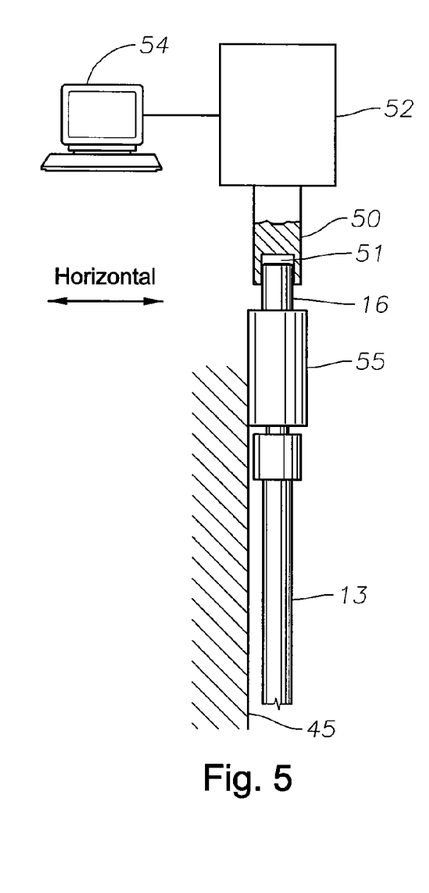
FIG. 5 is a diagrammatic representation of another embodiment of a system for preconditioning an illuminator.

In another embodiment, an endo-illuminator can be preconditioned using a vertical arrangement. The force of gravity on cannula 16 is a sufficient force with which to move cannula 16. FIG. 5 is a diagrammatic representation of a heating fixture with a vertical arrangement. According to one embodiment, an alignment tube 55 can be prealigned with heating member 50. Alignment tube 55 includes an opening through which cannula 16 can at least partially pass such that the distal end of cannula 16 is aligned with the opening 51 of heating member 50. There can be enough clearance between alignment tube 55 and cannula 16 to allow cannula 16 to move down as the distal end of distal fiber 20 softens. Heating member 50 can be coupled to a computer controlled translation stage 52 that allows heating member 50 to translate along at least one axis for positioning. A computer 54 can control movement of stage 52.

In operation, heating member 50 is heated to a desired temperature and translated downward (or cannula 16 translated upwards) such that the distal end of cannula 16 is inserted in heating member 50 to a desired insertion depth. Heating member 50 can heat cannula 16 for a desired time. As the distal portion of distal fiber 20 shrinks axially, gravity will cause optical element 26 to remain in contact with the distal end of distal fiber 20, but not cause so much force as to result in unacceptable amounts of concavity in the distal end of distal fiber 20.

The preconditioning parameters for a given heating element 50 and illuminator include the temperature of the element, insertion depth of the cannula 16, the dwell time (amount of time cannula 16 is inserted in heating element 50) and amount of force applied to maintain contact between the optical element 26 and distal fiber 20. Whether a particular set of preconditioning parameters are acceptable can be based on whether the endo-illuminator can experience a greater flux without catastrophic failure after preconditioning and whether any decrease in optical performance due to preconditioning is acceptable. By way of example, but not limitation, the following recipes have been found to create acceptable endo-illuminators:

For a 23 gauge wide angle illuminator probe using a heating element 50 with an opening having an inner diameter of 0.100" to 0.200":

376 degree set point
0.1" insertion depth
18-40 seconds dwell time
Insertion occurs with heating element at 400 deg F. actual temperature with temperature on the rise.

For a 25 gauge wide angle illuminator probe using a heating element 50 with an opening with an inner diameter of 0.100" to 0.200":

376 degree set point
0.1" insertion depth
6-12 seconds dwell time
Insertion occurs with heating element is at 400 deg F. actual temperature with temperature on the rise.

In the embodiments discussed above, the distal portion of cannula 16 and optical element assembly 32 is heated using an external heating element 50. This, in turn, causes the distal portion of distal fiber 20 to heat and soften. According to another embodiment, however, preconditioning can be performed using high intensity light. According to this embodiment, the endo-illuminator without the handpiece and without distal fiber 20 adhered to cannula 16 can be subjected to high intensity light, such as xenon or other light. This can cause heating and softening of the distal portion of distal fiber 20. If a small force, such as the force of gravity, is applied to the cannula 16 in the direction of axial shrinkage of the fiber, cannula 16 will move with the axially shrinking distal portion. Consequently, the optical element 26 will remain in contact with the distal end of the distal optical fiber 20. This can allow the residual stress in the distal portion of the distal optical fiber 20 to be released while maintaining zero gap between the optical element 26 and the distal end of distal fiber 20.

Preconditioning of distal fiber 20 causes the fiber to adhere to the cannula due to lateral swelling of the fiber to fill the inner diameter of the cannula and the sticking of tacky cladding material to the cannula. This can eliminate the need to adhere the proximal portion of cannula 16 to distal fiber 20. In other embodiments, the proximal portion of cannula 16 can be adhered to distal fiber 20 using a suitable adhesive such as Loctite 4014 by the Henkel Loctite Corporation of Rocky Hill, Conn.

Figure 6:
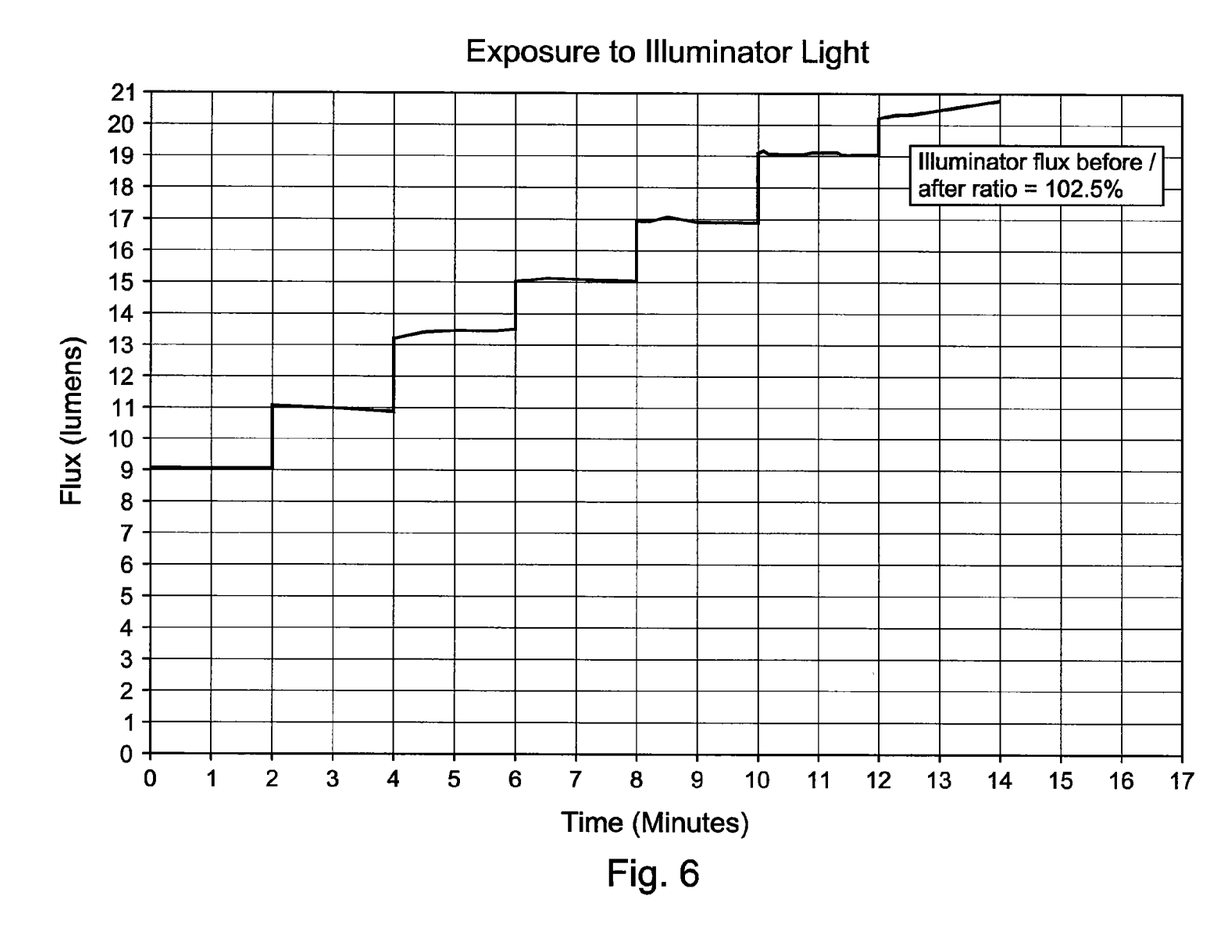
FIG. 6 is a graph illustrating resistance to run-away thermal deformation due to preconditioning.
Figure 7:
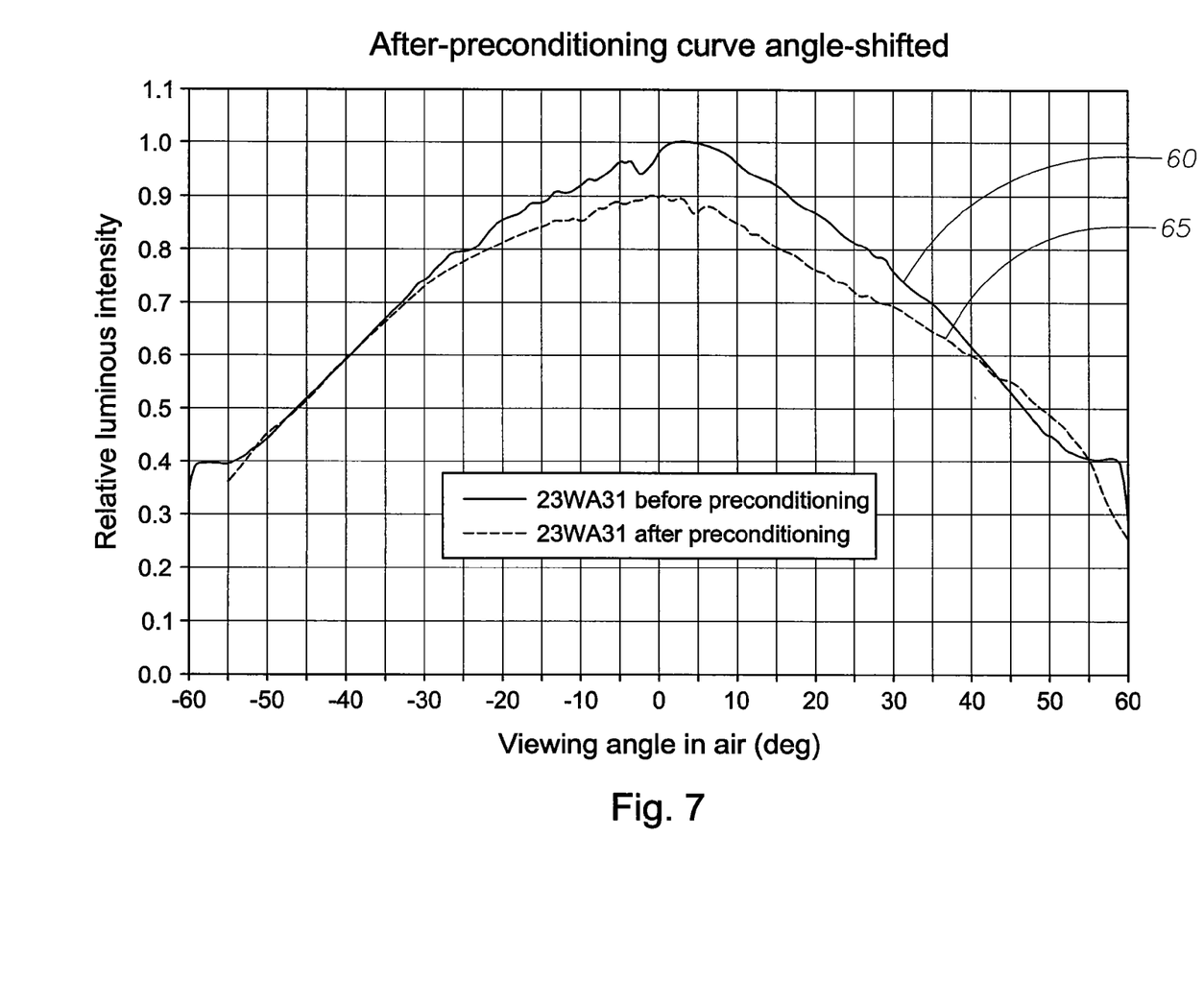
FIG. 7 is a graph illustrating optical performance for a preconditioned versus non-preconditioned illuminator.
Figure 8:
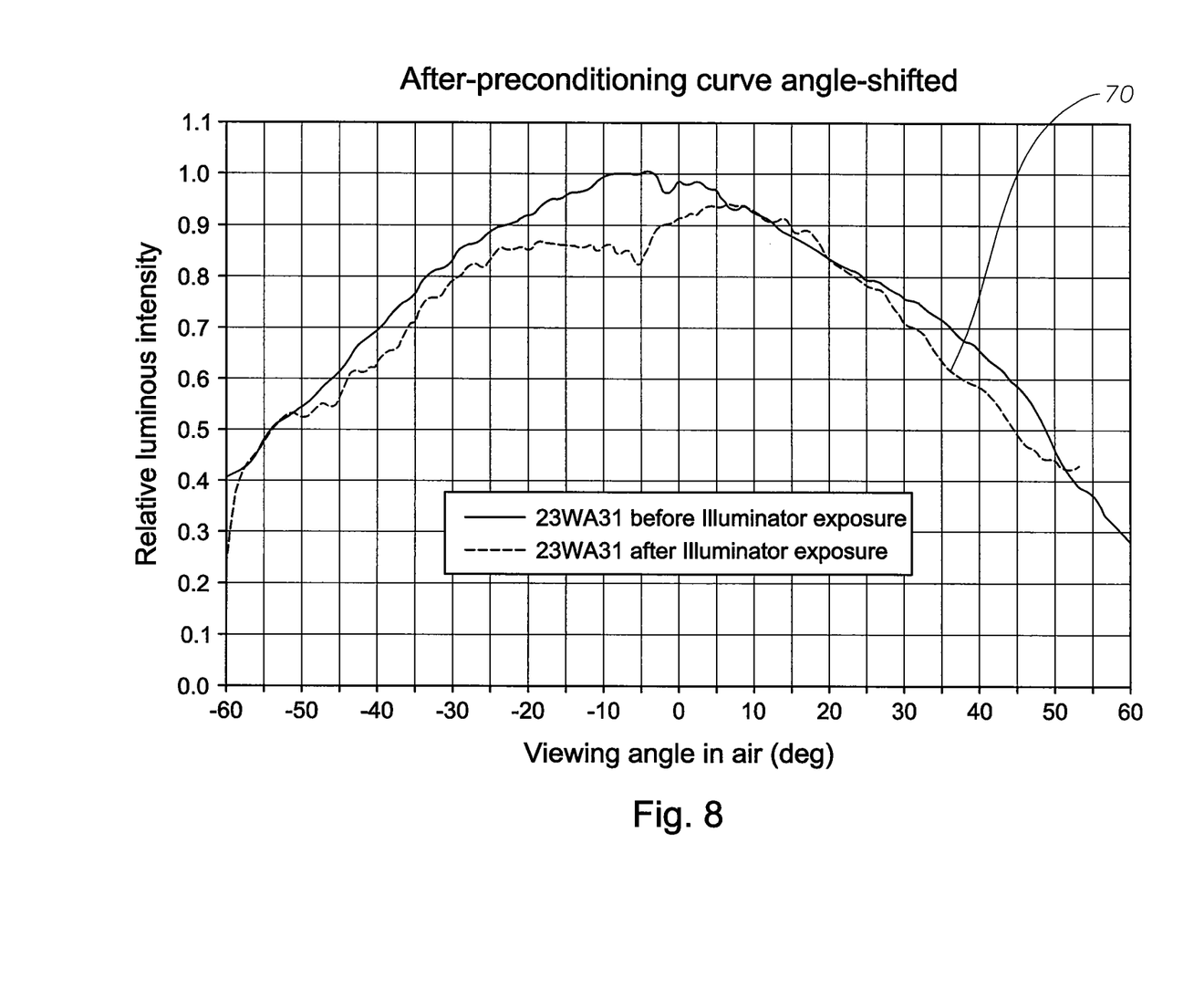
FIG. 8 is another graph illustrating optical performance for a preconditioned versus non-preconditioned illuminator.

Preconditioning of distal fiber 20 relieves the axial stress stored in the fiber and reduces the susceptibility of the fiber to thermal deformation from subsequent exposure to high intensity light. Data shows that the flux can be increased greatly when compared to FIG. 3 without catastrophic failure if the distal portion of distal fiber 20 has been preconditioned as described above. FIG. 6, for example, illustrates data from a 23 gauge wide angle illuminator that was preconditioned using xenon light. Preconditioning using a heating member provides similar results. The decreased susceptibility of the fiber to thermal deformation is accomplished with little decrease in optical performance. FIG. 7 illustrates relative luminous intensity versus viewing angle in air of a 23 gauge wide angle illuminator without preconditioning (line 60) and with preconditioning (line 65) using a heating element. FIG. 8 shows a similarly modest decrease in optical performance when preconditioning is done using xenon light (line 70) versus the 23 gauge wide angle illuminator without preconditioning.

In the above examples, preconditioning occurs after distal optical fiber 20 is coupled to proximal optical fiber 13. In other embodiments, preconditioning of distal optical fiber 20 can occur first. Additionally, similar preconditioning can be performed on devices that utilize only one optical fiber or one gauge of optical fiber. Furthermore, while distal optical fiber 20 is discussed in terms a single fiber, distal optical fiber 20 can be a collection of smaller optical fibers.

As used herein, the terms "comprises," "comprising," "includes," "including" "has," "having" or any other variation thereof, are intended to cover a non-exclusive inclusion. For example, a process, process, article, or apparatus that comprises a list of elements is not necessarily limited only those elements but may include other elements not expressly listed or inherent to such process, process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead these examples or illustrations are to be regarded as being described with respect to one particular embodiment and as illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such non-limiting examples and illustrations includes, but is not limited to: "for example", "for instance", "e.g.", "in one embodiment".

What is claimed is:

1. A wide-angle illuminator comprising:
    a cannula defining a passage;
    an optical element disposed at an end of the cannula;
    an optical fiber comprising a distal end, the optical fiber running through the passage defined in the cannula, wherein the optical fiber includes at least a heat preconditioned distal portion that terminates in the distal end and wherein the distal end is in contact with the optical element, the heat preconditioned distal portion, having a lower level of residual stress than an adjacent portion of the optical fiber.

2. The wide-angle illuminator of claim 1, wherein the optical element is a sapphire lens.

3. The wide-angle illuminator of claim 1, wherein the optical fiber is a distal fiber coupled to a proximate fiber.

4. The wide-angle illuminator of claim 3, wherein the distal fiber is one of a 23 or a 25 gauge optical fiber.

5. The wide-angle illuminator of claim 3, wherein the proximal optical fiber is coupled to a light source using an SMA optical fiber connector.

6. The wide-angle illuminator of claim 5, wherein the light source is a xenon light source.

7. The wide-angle illuminator of claim 1, wherein the cannula is one of a 23 gauge or 25 gauge cannula.

8. The wide-angle illuminator or claim 1, wherein the optical element comprises a flat surface and wherein the flat surface of the optical element is disposed at a distal end of the optical element.

9. The wide-angle illuminator of claim 1, wherein the optical element comprises a flat surface and wherein the flat surface of the optical element is co-incident with an open aperture at a distal end of the cannula.

10. A wide-angle illuminator comprising:
    a cannula defining a passage;
    an optical element disposed at an end of the cannula, the optical element comprising a surface, at least a portion of the surface of the optical element defining a distal end of the wide-angle illuminator;
    an optical fiber comprising a distal end, the optical fiber running through the passage defined in the cannula, wherein the optical fiber includes at least a heat preconditioned distal portion that terminates in the distal end and wherein the distal end is in contact with the optical element, the heat preconditioned distal portion having a lower level of residual stress than an adjacent portion of the optical fiber.

11. The wide-angle illuminator of claim 10, wherein the optical element is a sapphire lens.

12. The wide-angle illuminator of claim 10, wherein the optical fiber is a distal fiber coupled to a proximate fiber.

13. The wide-angle illuminator of claim 12, wherein the distal fiber is one of a 23 or a 25 gauge optical fiber.

14. The wide-angle illuminator of claim 12, wherein the proximal optical fiber is coupled to a light source using an SMA optical fiber connector.

15. The wide-angle illuminator of claim 14, wherein the light source is a xenon light source.

16. The wide-angle illuminator of claim 10, wherein the cannula is one of a 23 gauge or 25 gauge cannula.

17. The wide-angle illuminator of claim 10, wherein at least a portion of the surface of the optical element is co-incident with an open aperture of the cannula.

18. The wide-angle illuminator of claim 10, wherein the surface of the optical element comprises a flat surface.

19. The wide-angle illuminator of claim 18, wherein the flat surface defines the distal end of the wide-angle illuminator.

20. The wide-angle illuminator of claim 18, wherein the flat surface is co-incident with an open aperture at a distal end of the cannula.

\* \* \* \* \*